United States Patent
Kumagai

[11] Patent Number: 6,031,933
[45] Date of Patent: Feb. 29, 2000

[54] METHOD AND APPARATUS FOR INSPECTING THE OUTER APPEARANCE OF A GOLF BALL

[75] Inventor: Hiroki Kumagai, Chichibu, Japan

[73] Assignee: Bridgestone Sports Co., Ltd., Tokyo, Japan

[21] Appl. No.: 08/840,640

[22] Filed: Apr. 25, 1997

[30] Foreign Application Priority Data

Apr. 25, 1996 [JP] Japan .................................. 8-129125

[51] Int. Cl.[7] ...................................................... G06K 9/00
[52] U.S. Cl. ........................... 382/141; 73/865.8; 356/426
[58] Field of Search ................................. 382/141, 100, 382/152, 143; 73/865.8, 12.02; 356/426, 237; 348/86, 92, 125, 128

[56] References Cited

U.S. PATENT DOCUMENTS

| | | | |
|---|---|---|---|
| 5,517,027 | 5/1996 | Nakagawa et al. | 250/306 |
| 5,568,250 | 10/1996 | Nishiyama et al. | 356/28 |
| 5,703,687 | 12/1997 | Kumagai et al. | 356/426 |
| 5,777,244 | 7/1998 | Kumagai et al. | 73/865.8 |

*Primary Examiner*—Leo H. Boudreau
*Assistant Examiner*—Bhavesh Mehta
*Attorney, Agent, or Firm*—Sughrue, Mion, Zinn, Macpeak & Seas, PLLC

[57] ABSTRACT

The outer appearance of a golf ball (1) having a multiplicity of dimples (9) in its surface is inspected for detecting a defect (10) on the ball surface, by illuminating light to the golf ball (1), rotating the golf ball at a constant speed in one direction, operating a line sensor camera (4) to take a series of plurality of line images of the ball surface along a line (b) perpendicular to the rotational direction (a), the camera delivering image data including the line images, constructing a two-dimensional image from the image data, converting a brightness change appearing in the two-dimensional image in the rotational direction of the ball into a variation per preset unit, and subjecting the resulting variation data to binary processing on the basis of a threshold set between the variation associated with the dimple (9) and the variation associated with the defect (10), thereby detecting whether or not the defect (10) is present.

5 Claims, 8 Drawing Sheets

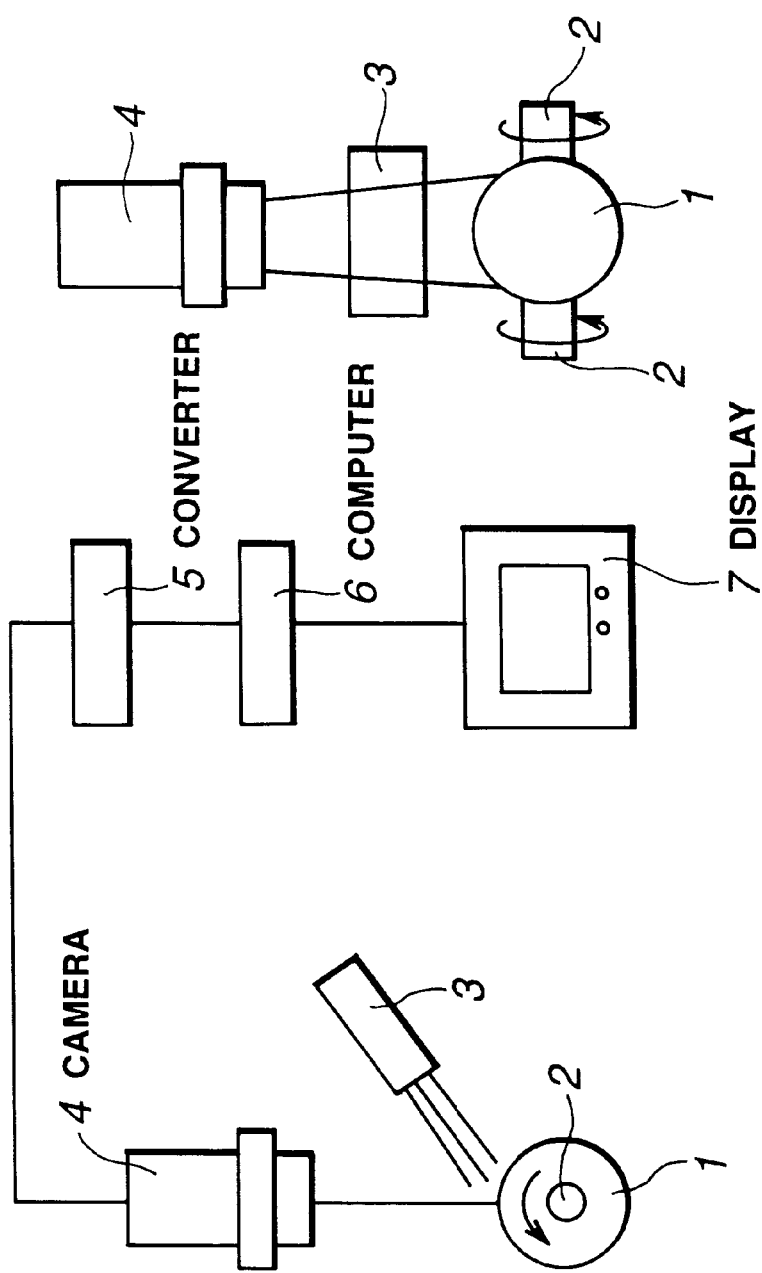
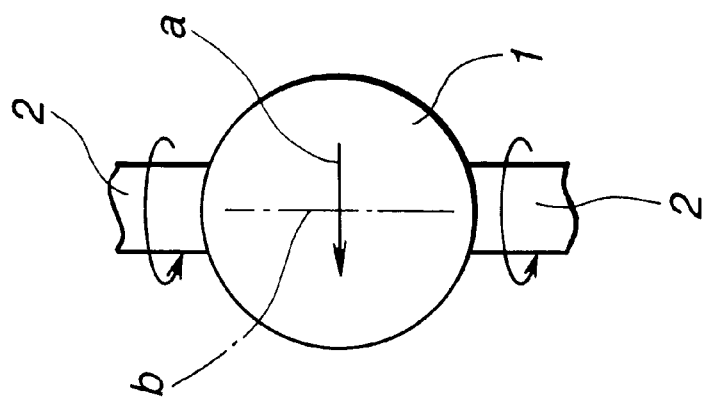
FIG.1A FIG.1B FIG.1C

METHOD AND APPARATUS FOR INSPECTING THE OUTER APPEARANCE OF A GOLF BALL

BACKGROUND OF THE INVENTION

1. Field of the Invention

This invention relates to a method and apparatus for inspecting the outer appearance of a golf ball having a multiplicity of dimples in its surface for detecting a defect on the ball surface. More particularly, it relates to a golf ball outer appearance inspecting method and apparatus capable of automatic, high-precision judgment whether or not golf ball products are to be rejected.

2. Prior Art

In the manufacture of golf balls, defects such as flaws, weld marks, gate marks (depressions left at the gate), and foreign matter inclusions can form on the surface of golf balls for some reason or another. Golf balls having such a defect are low in commodity value and will suffer from a loss of aerodynamic performance such as a short carry and less flight stability because the defect can induce turbulence during flight. It is then a common practice to carry out an outer appearance inspection on golf balls for picking up defective balls before shipping.

It has long been desired to incorporate an inspection apparatus in the manufacturing line to automate an outer appearance inspection for detecting any defect on the golf ball surface. Automatic outer appearance inspection is difficult with golf balls because of their unique surface topography. The present status of outer appearance inspection is visual observation by workers.

As a substitute for visual inspection, it is commonly employed to automatically inspect the outer appearance of various articles by taking an optical image of an object to be inspected by optical imager means such as a camera, and judging from the image determining whether or not the outer appearance is acceptable by image processing means. Where the object to be inspected is a dimpled golf ball which is a spherical article having a plurality of depressions in its surface, it is difficult to detect a defect on the surface. Since dimples are distributed on the spherical surface, the dimples appear in the image of the surface as ellipsoids having indefinite major and minor axes and additionally, these ellipsoids appear irregularly. It is then quite difficult to detect the difference between the dimple and the defect on the image for judging the presence of the defect. Precise inspection is thus prohibited.

Since golf balls are generally molded in molds, it is a common practice to apply to golf balls an indentation mark indicating a particular mold for the purpose of identifying the mold in which a ball is produced. Such an indentation mark is generally applied within a dimple. Unlike a stamp mark printed in color, the indentation mark is a symbol represented by a colorless raised or depressed portion. It is difficult to discriminate the indentation mark from the defect.

It is also contemplated to detect a change on the ball surface using a laser beam. The inspection with a laser beam adds to the cost and is thus inapplicable to golf balls which are of low price and require mass inspection within a short time.

For this reason, the state-of-the-art outer appearance inspection of golf balls relies on visual observation by workers as mentioned above. The inspection by visual observation imposes a heavy burden to workers. To visually find a slight defect on a golf ball having a plurality of dimples in its surface is a very hard work. Since the precision of judgment varies with individual workers and with the condition of a worker, sufficient precision of inspection is not always insured.

SUMMARY OF THE INVENTION

An object of the present invention is to provide a method and apparatus for inspecting the outer appearance of a golf ball which can automatically and precisely detect any defect on the ball surface to judge whether or not the golf ball is rejected.

In a first aspect, the present invention provides a method for inspecting the outer appearance of a golf ball having a multiplicity of dimples in its surface for detecting a defect on the ball surface, comprising the steps of illuminating light to a selected region of the golf ball, rotating the golf ball at a constant speed in one direction, operating a line sensor camera to take a series of plurality of line images of the ball surface in the selected region along a line perpendicular to the rotational direction at the same time as the illuminating and rotating steps, the camera delivering image data including the line images, constructing a two-dimensional image from the image data, converting a brightness change appearing in the two-dimensional image in the rotational direction of the ball into a variation per preset unit, thereby obtaining variation data, and subjecting the variation data to binary processing on the basis of a threshold set between the variation associated with the dimple and the variation associated with the defect, thereby detecting whether or not the defect is present.

According to the inspection method of the invention, the line sensor camera is first operated to take a series of plurality of line images of the ball surface while light is illuminated to the golf ball rotating at a constant speed in one direction. A two-dimensional image of the ball surface is obtained from the image data including the line images delivered from the camera. The golf ball surface consists of a spherical land (where no dimples are present) and dimples presenting a concave curved surface. The land appears on the two-dimensional image at uniform brightness since the angle between the illuminating light and the land surface remains constant during rotation of the ball. On the other hand, the dimple appears on the two-dimensional image as a gradation of brightness continuously changing along the rotational direction of the ball since the angle between the illuminating light and the dimple surface gradually changes as the ball rotates. A flaw, if any, appears as an abrupt brightness change on the tow-dimensional image. The term "defect" is used to encompass flaws, weld marks, gate marks (depressions left at the gate), and foreign matter inclusions on the golf ball surface.

Next, changes of brightness appearing on the tow-dimensional image along the rotational direction of the ball are converted into variations per preset unit. The land provides little variation because of little brightness change. The dimple affords a gradual change of brightness even though the final change of brightness is considerably large and hence, a variation per preset unit is small. In contrast, the flaw affords an abrupt brightness change although its brightness is equal to the final brightness of the dimple and hence, a variation per preset unit is very large.

According to the invention, the thus obtained variation data are binary processed on the basis of a threshold set between the variation of the dimple and the variation of the defect, thereby detecting the presence of the defect. The ball surface is judged to contain no defect if there is no value of variation in excess of the threshold, but to contain a defect if there is a value of variation in excess of the threshold.

In this way, the outer appearance inspecting method of the invention detects any defect on the surface of a golf ball by taking an image of a rotating golf ball by means of a line sensor camera, constructing a two-dimensional image from the image data, and converting a change of brightness appearing on the two-dimensional image into a variation of brightness per preset unit in the rotational direction of the ball, thereby converting the dimple and the defect into bits of information having a discriminatable difference.

The outer appearance inspecting method of the invention ensures to detect any defect on the surface of a golf ball by precisely discriminating the defect from the dimples on the ball surface. As previously mentioned, certain golf balls have an indentation mark in a dimple. Since such an indentation mark consists of small protrusions or depressions, the indentation mark appears as an abrupt change of brightness on the two-dimensional image. Then brightness variations associated with the indentation mark are hardly discriminatable from those associated with the defect. Then in the case of a golf ball having such an indentation mark, it is difficult to detect only the defect by the above-mentioned inspection method.

Then in a second aspect, the present invention provides an inspection method that can detect only a defect on a golf ball having an indentation mark. Specifically, the invention provides a method for inspecting the outer appearance of a golf ball having a multiplicity of dimples in its surface for detecting a defect on the ball surface, comprising the steps of illuminating light to a selected region of the golf ball, rotating the golf ball at a constant speed in one direction, operating a line sensor camera to take a series of plurality of line images of the ball surface in the selected region along a line perpendicular to the rotational direction at the same time as the illuminating and rotating steps, the camera delivering image data including the line images, constructing a two-dimensional image from the image data, converting a brightness change appearing in the tow-dimensional image in the rotational direction of the ball into a variation per preset unit, thereby obtaining variation data, and subjecting the variation data to binary processing on the basis of a first threshold set between the variation associated with the dimple and the variation associated with the defect, thereby obtaining first image data representing the defect as a light or dark area, subjecting the variation data to binary processing on the basis of a second threshold set between the variation associated with the land and the variation associated with the dimple, thereby obtaining an image representing the defect and dimples as light or dark areas in a dark or light background, subjecting the last-mentioned image to image processing, the image processing including the steps of expanding the defect and dimple-representing areas, contracting the defect and dimple-representing areas to extinguish the defect-representing area, and expanding again the dimple-representing areas to the original size, thereby obtaining second image data representing only the dimples as light or dark areas, overlapping the first image data and the second image data with the light and dark areas being reversed for one of the first image data and the second image data, and processing the overlapped data such that either one of light and dark areas is preferentially selected when light and dark areas are overlapped, thereby extinguishing areas other than the defect-representing area from the first image data, thereby detecting only the defect.

As in the first method, the second inspecting method of the invention detects any defect on the surface of a golf ball by taking an image of a rotating golf ball by means of a line sensor camera, constructing a two-dimensional image from the image data, and converting a change of brightness appearing on the two-dimensional image into a variation of brightness per preset unit in the rotational direction of the ball. According to the second method, among data detected by binary processing as representing brightness variations in excess of the threshold, those data associated with the indentation are selectively erased, thereby detecting only the defect.

As in the first method, the second inspecting method of the invention detects any defect on the surface of a golf ball by converting a change of brightness appearing on the two-dimensional image obtained from a line sensor camera image of a rotating golf ball into a variation of brightness per preset unit in the rotational direction of the ball to yield variation data and binary processing the variation data. The sites on the ball surface detected by the binary processing as representing brightness variations in excess of the threshold include the indentation as well as the defect. Then, according to the second inspection method, the first image data wherein the defect and the indentation are represented as light or dark areas by the binary processing is obtained while the variation data is subject to binary processing by setting a second threshold between the variation associated with the land and the variation associated with the dimple. There is obtained an image wherein the dimples and the defect are represented as light or dark areas. The image is processed such that the areas representing the defect and dimples are expanded, then once contracted to extinguish the defect-representing area, and thereafter expanded again until the dimple-representing areas resume the original size, thereby obtaining second image data representing only the dimples as light or dark areas. While the light and dark areas of either one of the first image data and the second image data are reversed, the first image data and the second image data are overlapped each other. When light and dark areas are overlapped between the first and second data, either one of light and dark areas is preferentially selected. As a result, the data except for the defect-representing data are extinguished from the first image data. Only the defect is detected in this way.

The operation of erasing the indentation-representing data is described in detail. The variation data is subject to binary processing by setting a second threshold between the variation associated with the land and the variation associated with the dimple. Then, there is obtained an image wherein the dimples and the defect presenting a greater variation than the dimple are represented as light or dark areas. Where there is an indentation in a dimple, the indentation presents an equal variation to the defect, has the identical lightness with the dimple and is thus hidden in the dimple. Particularly when the indentation is a raised portion, the indentation will present smaller variations like the land and appear as a light or dark area in the dimple.

Next, the light or dark areas representing the dimples and the defect on the image are expanded to extinguish the indentation which has been represented within the dimple. Then the light or dark areas representing the dimples and the defect are contracted until the defect is extinguished and thereafter, expanded again until the dimples resume their original size. As a result of this expansion and contraction procedure, the indentation and the defect are extinguished, and there is obtained a second image (or second image data) wherein only the dimples are represented as light or dark areas.

Then the light and dark areas of either the first image (data) or the second image (data) are reversed. The second image (data) is laid on the first image (data) wherein the indentation and defect are represented as light or dark areas. The algorithm is designed so as to give preference to either light or dark area where light and dark areas overlap. For instance, if the second image (data) wherein only the dimples are represented as white areas in the black background is laid on the first image (data) wherein the indentation and defect are represented as black areas in the white background, then the indentation (black) in the first image data overlaps the dimple (white) in the second image data, the defect (black) of the first image data overlaps the black background of the second image data, and the white background of the first image data overlaps the dimples or black background of the second image data as shown in Table 1. In this state, the algorithm is designed so as to give preference to white where while and black areas overlap. Then, as shown in Table 1, all the areas become white except for the defect of black-black combination.

TABLE 1

|  | First image data | Second image data (reversed) | After white preference processing |
|---|---|---|---|
| Land | white | black | white |
| Dimple | white | white | white |
| Defect | black | black | black |
| Indentation | black | white | white |

This results in an image (image data) wherein only the defect is represented as a black area in the white background. That is, among the defect and indentation detected by the binary processing based on the first threshold, the indentation is extinguished and only the defect is detected through the above-mentioned series of image processing steps. Therefore, if a variation in excess of the first threshold is contained in the first image data after the image processing, then the ball surface is judged to contain a defect.

In this way, the second inspection method permits only a defect to be detected on a golf ball having an indentation in a dimple since the indentation is extinguished from the first image data. When similar processing is done on a golf ball having no indentation, the detection of a defect is not adversely affected.

Often, characters and marks representing a trade name and player number are printed on the golf ball. Such a mark constitutes a part of large variations among the variation data. Without an expedient, the mark can be detected by binary processing as is the defect. As compared with dimples and a defect which are regarded mere concave depressions in the white background, a mark printed in black, blue or red appears as a portion with a very low brightness on the two-dimensional image. If a portion with a brightness below a certain level appearing on the tow-dimensional image is removed from the region to be inspected, then the mark is excluded from the object to be detected.

In a further aspect, the invention provides an apparatus for inspecting the outer appearance of a golf ball having a multiplicity of dimples in its surface for detecting a defect on the ball surface, comprising a rotating means for holding and rotating the golf ball at a constant speed in one direction, a lighting means for illuminating light to a selected region of the golf ball, a line sensor camera adapted to take a series of plurality of line images of the ball surface in the selected region along a line perpendicular to the rotational direction, the camera delivering image data including the line images, a one to two-dimensional image converter means for constructing a two-dimensional image from the image data, an image converter means for converting a brightness change appearing in the two-dimensional image in the rotational direction of the ball into a variation per preset unit, and an image analysis means for subjecting the variation data to binary processing on the basis of a threshold. The line sensor camera is operated to take a series of plurality of line images of the ball surface in the selected region along a line perpendicular to the rotational direction while light is illuminated to the selected region of the golf ball by the lighting means and the golf ball is rotated at a constant speed in one direction by the rotating means. The camera delivers image data including the line images to the one to two-dimensional image converter means, which constructs a two-dimensional image from the image data and delivers the image to the image converter means, which in turn, converts a brightness change appearing in the two-dimensional image in the rotational direction of the ball into a variation per preset unit and delivers the variation data to the image analysis means, which performs binary processing of the variation data on the basis of a threshold set between the variation associated with the dimple and the variation associated with the defect, thereby detecting whether or not the defect is present on the golf ball surface.

In a still further aspect, the invention provides an apparatus for inspecting the outer appearance of a golf ball having a multiplicity of dimples in its surface for detecting a defect on the ball surface, comprising a rotating means for holding and rotating the golf ball at a constant speed in one direction, a lighting means for illuminating light to a selected region of the golf ball, a line sensor camera adapted to take a series of plurality of line images of the ball surface in the selected region along a line perpendicular to the rotational direction, the camera delivering image data including the line images, a one to two-dimensional image converter means for constructing a two-dimensional image from the image data, an image converter means for converting a brightness change appearing in the two-dimensional image in the rotational direction of the ball into a variation per preset unit, an image analysis means for subjecting the variation data to binary processing on the basis of a threshold, and an image processing means for receiving the two-dimensional image consisting of light and dark areas and expanding and contracting the light or dark areas. The line sensor camera is operated to take a series of plurality of line images of the ball surface in the selected region along a line perpendicular to the rotational direction while light is illuminated to the selected region of the golf ball by the lighting means and the golf ball is rotated at a constant speed in one direction by the rotating means. The camera delivers image data including the line images to the one to two-dimensional image converter means, which constructs a two-dimensional image from the image data and delivers the image to the image converter means, which in turn, converts a brightness change appearing in the two-dimensional image in the rotational direction of the ball into a variation per preset unit and delivers the variation data to the image analysis means, which performs binary processing of the variation data on the basis of a threshold set between the variation associated with the dimple and the variation associated with the defect to thereby produce first image data representing the defect on the ball surface as a light or dark area. The image analysis means also performs binary processing of the variation data on the basis of a second threshold set between the variation associated with the land and the variation associated with the dimple to thereby produce an image representing the defect and dimples as light or dark areas, and delivers the last-mentioned image to the image processing means, which performs image processing including the steps of expanding the defect- and dimple-representing areas, contracting the defect- and dimple-representing areas to extinguish the defect-representing area, and expanding again the dimple-representing areas to the original size, thereby producing second image data representing only the dimples as light or dark areas. The apparatus further includes a processing means for overlapping the first image data and the second image data with the light and dark areas being reversed for one of the first image data and the second image data, and processing the overlapped data such that either one of light and dark areas is preferentially selected when light and dark areas are overlapped, thereby extinguishing areas other than the defect-representing area from the first image data, thereby detecting only the defect.

BRIEF DESCRIPTION OF THE DRAWINGS

The invention will be more readily understood by reading the following description taken in conjunction with the accompanying drawings.

FIGS. 1A–1C schematically illustrates an apparatus for inspecting the outer appearance of a golf ball according to the method of the invention.

DESCRIPTION OF THE PREFERRED EMBODIMENTS

Figure 2A:
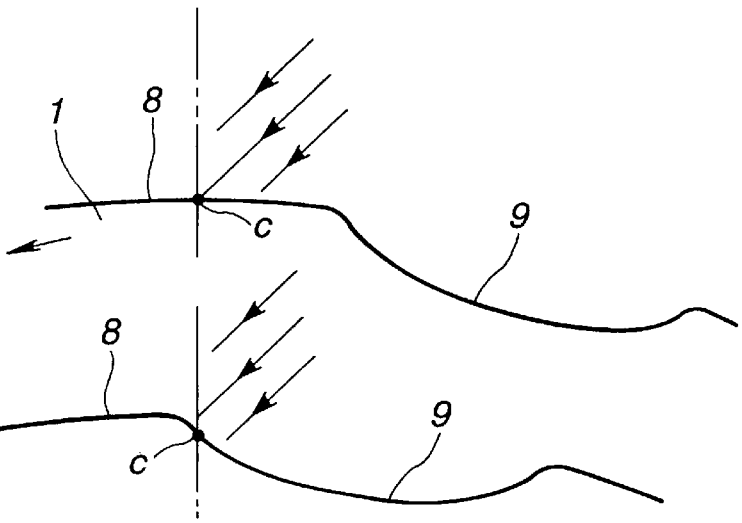
FIG. 2 illustrates the relationship of illuminating light to a rotating golf ball at an imaging position by a line sensor camera.
Figure 2B:
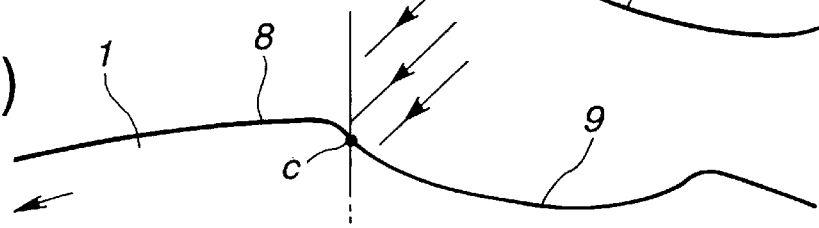
Figure 2C:
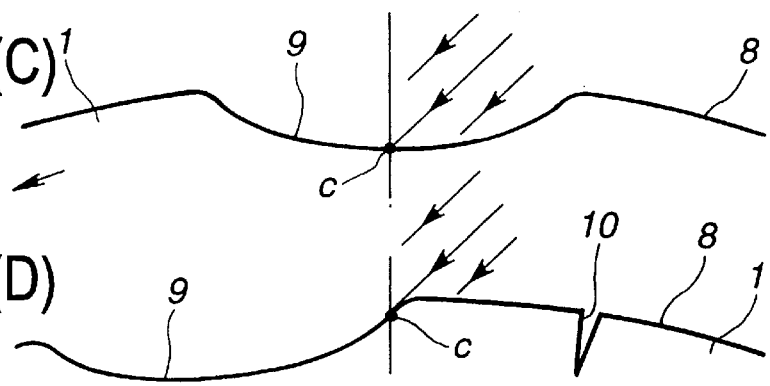
Figure 2D:
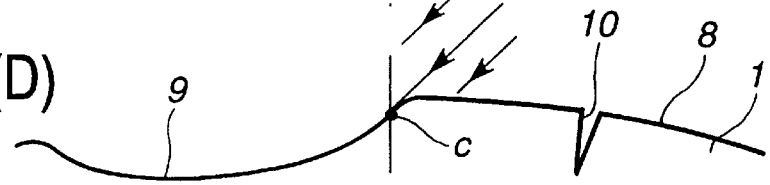
Figure 2E:
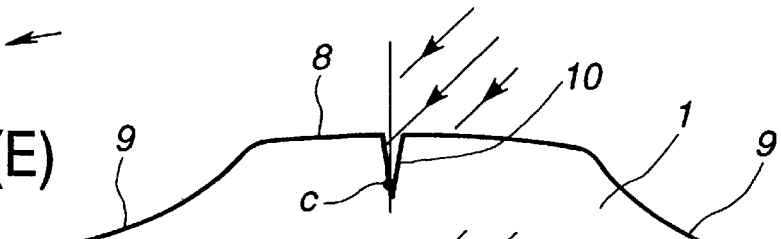
Figure 2F:
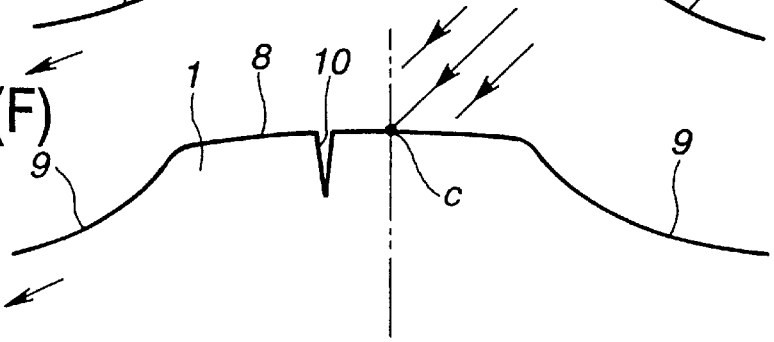

Now, the preferred embodiment of the invention is described. The golf ball surface includes a multiplicity of dimples and a land which is a ball surface portion where no dimples are formed. A defect on the ball surface is typically given by a flaw.

FIGS. 1A–1C schematically illustrates an apparatus for inspecting the outer appearance of a golf ball according to one embodiment of the invention. A golf ball to be inspected is designated at 1. Means for rotating the golf ball includes a pair of clamping/rotating shafts 2, 2 for clamping the golf ball 1 at its diametrical ends and rotating the ball about the axis of the shafts. Lighting means 3 is disposed for illuminating light to a selected region of the golf ball 1. A line sensor camera 4 is adapted to take a line or one-dimensional image of the golf ball surface in the selected region. Converter means 5 is used to convert the one-dimensional image into a two-dimensional image. A computer 6 includes image converter means, image analysis means and image processing means for applying various image processes to the two-dimensional image for analyzing the image. A monitor 7 is used to display the image. It is noted that another pair of rotating shafts are disposed in a direction perpendicular to the rotating shafts 2, 2 though not shown.

This outer appearance inspection apparatus is designed to detect a defect, typically a flaw on the surface of a golf ball by illuminating light from the lighting means 3 to a selected region of the golf ball 1. The golf ball 1 is rotated about the shaft axis at a constant speed in one direction by means of the rotating shafts 2. The line sensor camera 4 is operated to take a series of plurality of line images of the ball surface at the same time as the illuminating and rotating steps, the camera delivering image data including the line images. A two-dimensional image is constructed from the image data by means of the converter means 5. The two-dimensional image is subjected to various image processes for image analysis, thereby detecting the defect, typically a flaw on the ball surface. The resulting image is displayed on the monitor 7. The line sensor camera 4 is set to take a picture along a line (designated by dot-and-dash line b) perpendicular to the rotating direction of the ball 1 designated by arrow a as shown in FIG. 1(C).

Using the inspection apparatus mentioned above, the outer appearance of a golf ball is inspected by the first inspection method according to the invention as follows. First, while light is illuminated to the selected region of the golf ball 1 from the lighting means 3 and the golf ball 1 is rotated at a constant speed in one direction by the rotating shafts 2, the line sensor camera 4 is operated to take a series of plurality of line images of the ball surface in the selected region along the line b perpendicular to the rotational direction a of the ball. The camera 4 delivers one-dimensional image data including the line images to the converter means 5 which converts the data into a two-dimensional image as shown in FIG. 3.

Figure 3:
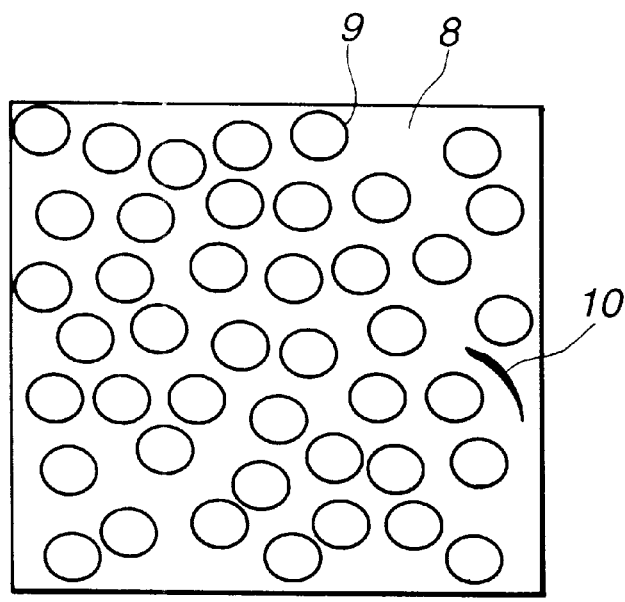
FIG. 3 illustrates a two-dimensional image.

As shown in FIG. 3, the two-dimensional image includes the land 8 of the ball surface as the background and dimples 9 and a flaw 10 represented by light or dark areas. As shown in FIG. 2, the line sensor camera 4 takes a picture of the ball surface at an imaging point c. Referring to FIG. 2, it is considered how the angle between light (shown by three arrows in FIG. 2) from the lighting means 3 and the ball surface at the image point c changes as the ball rotates. On the land, the angle is always constant (see FIGS. 2A and 2F). On the dimple 9 presenting a concave curved surface, the angle gradually changes (see FIGS. 2B, 2C and 2D). At the flaw 10, the angle experiences a temporary, but drastic change (see FIG. 2E).

Figure 4:
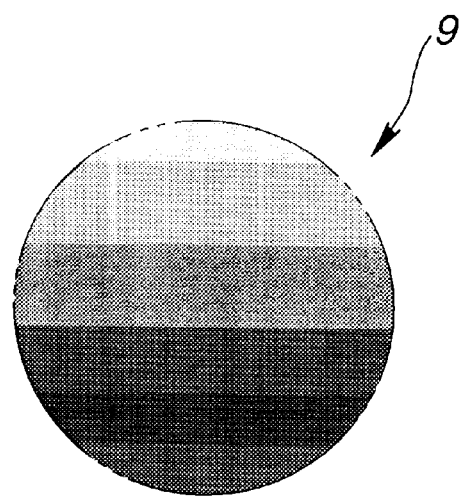
FIG. 4 is an enlarged view of a dimple portion in the two-dimensional image.

Therefore, the land which forms the fixed angle with the illuminating light appears at a constant brightness on the two-dimensional image. The dimple which forms a gradually changing angle with the illuminating light appears on the two-dimensional image as a gradation of brightness gradually changing along the rotational direction of the ball as shown in FIG. 4. The flaw appears as an abrupt brightness change on the two-dimensional image. Then in the resultant two-dimensional image of FIG. 3, the land 8 appearing at a constant brightness forms the background, the dimples 9 appear as graded brightness areas, and the flaw 10 appears as the abrupt brightness change area. It is noted that the change of brightness is illustrated stepwise in FIG. 4 for convenience sake although the dimple 9 actually appears as a gradation of continuously changing brightness.

Figure 5:
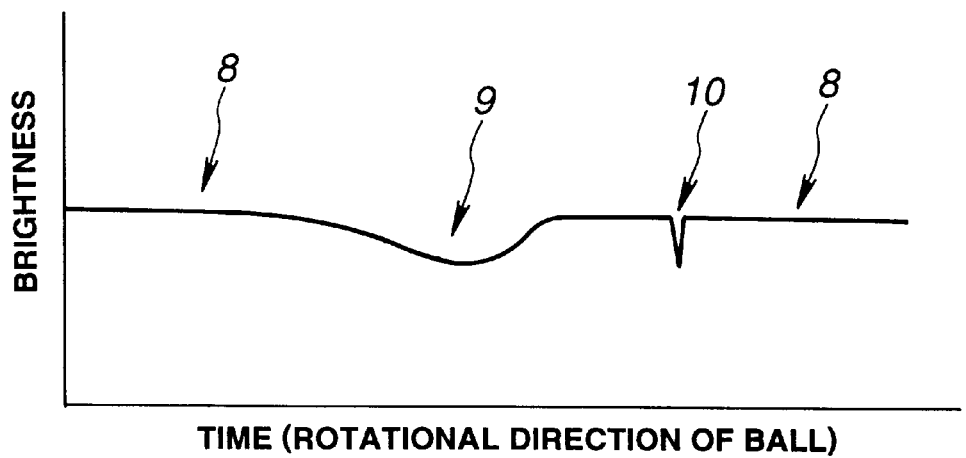
FIG. 5 is a graph showing a change of brightness in the two-dimensional image.

Next, the brightness change along the rotational direction of the ball appearing on the two-dimensional image is converted into a variation per preset unit. The land 8 affords little brightness change and hence, little variation. The dimple 9 affords a gradual change of brightness even though the final change of brightness is considerably large and hence, a variation per preset unit is small. In contrast, the flaw 10 affords an abrupt brightness change although the brightness is equal to the final brightness of the dimple 9 and hence, a variation per preset unit is very large. Now the brightness changes along the rotational direction of the ball appearing on the tow-dimensional image are plotted on a graph. Then, there is obtained a curve as shown in FIG. 5 wherein the brightness is approximately constant in the region of a land 8, gradually changes in the region of a dimple 9, becomes again approximately constant in the region of an adjacent land 8, and abruptly changes in the region of a flaw 10. The abrupt change in the region of flaw 10 forms a valley relative to the generally flat curve in the region of land 8. When the brightness change curve is converted into a variation per preset unit, the variation is approximately 0 in the land 8, small in the dimple 9, and large in the flaw 10.

Figure 6:
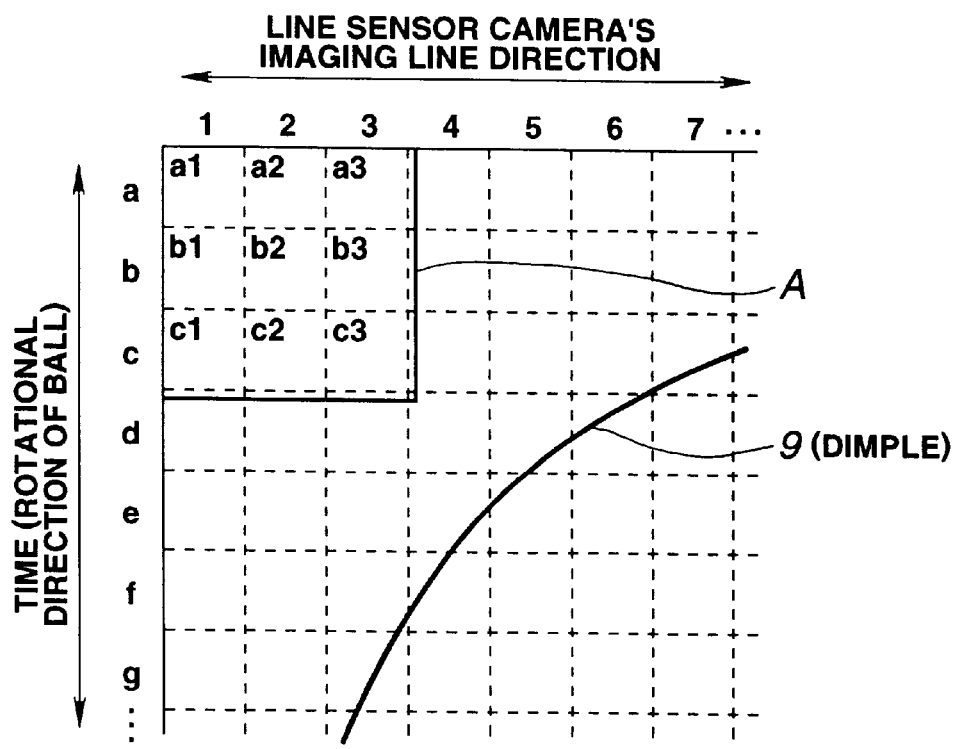
FIG. 6 illustrates a portion of the two-dimensional image.

The variation is determined per preset unit along the rotational direction of the ball. The unit on the basis of which the variation is determined is preset using pixels of the line sensor camera 4 as a basis unit. The line sensor camera 4 has a row of numerous (generally 1,000 to 5,000) pixels. The two-dimensional image obtained from the linear or one-dimensional images taken by the line sensor camera 4 consists of a series of pixels 1, 2, 3, 4, 5, . . . which are stacked in rows a, b, c, d, e, . . . in the rotational direction of the ball as shown in FIG. 6. Provided that a region A consisting of nine pixels a1 to a3, b1 to b3 and c1 to c3 is a unit, the difference between the sum of brightness of pixels a1 to a3 and the sum of brightness of pixels c1 to c3 is determined. This difference is considered a variation of brightness in region A. Similarly, a variation per unit is determined provided that a region consisting of nine pixels in three columns and three rows is a unit. It is understood that the number of pixels in a unit is not particularly limited although it is preferably from 2×2 pixels to about 5×5 pixels.

Figure 7:
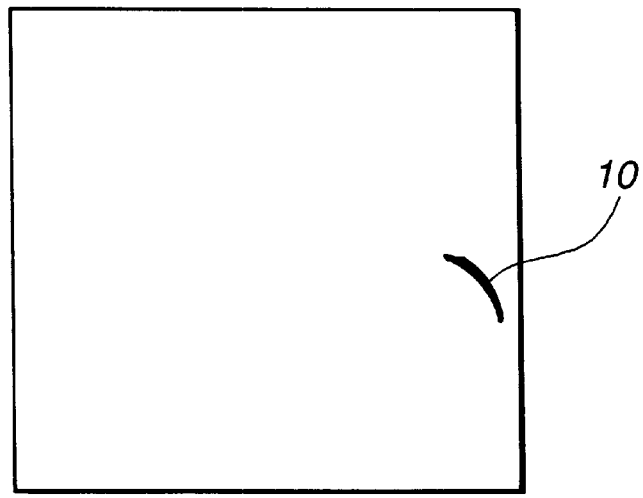
FIG. 7 is an image obtained by converting the tow-dimensional image into variation data and subjecting the variation data to binary processing.

Next, the variation data is subject to binary processing by setting a threshold between the variation associated with the dimple 9 and the variation associated with the flaw 10, thereby detecting the flaw 10. As a result of binary image processing, only the flaw 10 whose brightness variation exceeds the threshold is left on the two-dimensional image as shown in FIG. 7. If the variation data contains no value of variation in excess of the threshold, it is detected that no flaw is present. If the variation data contains a value of variation in excess of the threshold, it is detected that a flaw is present.

It is understood that the computer 6 automatically carries out the above-mentioned step of converting the brightness change appearing on the two-dimensional image along the rotational direction of the ball into a variation per preset unit and the above-mentioned step of binary processing the variation data for detecting a flaw. The computer 6 delivers the results of processing to the monitor 7 so that the image is displayed on the monitor 7. Also, the golf ball can be inspected over its entire surface by dividing the surface of the golf ball 1 into six surface sections corresponding to a regular hexagon and repeating the above-mentioned operation for each of the six surface sections. In this case, the golf ball 1 is supported by the second pair of rotating shafts (not shown), the clamping of the ball by the first pair of rotating shafts 2, 2 is once canceled, the ball is rotated 90° by the second pair of rotating shafts, the ball is again clamped by the first pair of rotating shafts 2, 2, and inspection operation is similarly performed. This enables two surface bands to be inspected with a single line sensor camera although such two surface bands cannot be otherwise photographed by a single line sensor camera.

Often, characters and marks representing a trade name and player number are printed on the golf ball. Such a mark constitutes a part of large variations among the variation data. Without an expedient, the mark can be detected by binary processing as is the flaw. As compared with dimples 9 and a flaw 10 which are regarded mere concave depressions in the white background, a mark printed in black, blue or red appears as a portion with a very low brightness on the two-dimensional image. If a portion with a brightness below a certain level appearing on the two-dimensional image is removed from the region to be inspected, then the mark is excluded from the object to be detected.

In this way, the first inspection method of the invention can convert a dimple 9 and a flaw 10 into bits of information having a discriminatable difference by taking pictures of a rotating golf ball 1 by means of the line sensor camera 4 to produce a two-dimensional image, and converting changes of brightness appearing on the tow-dimensional image into brightness variations per preset unit along the rotational direction of the ball. This insures correct detection of the flaw 10.

As previously mentioned, golf balls sometimes have an indentation mark borne in a dimple. Since such an indentation mark consists of small protrusions or depressions, the indentation mark appears as an abrupt change of brightness on the two-dimensional image. Then brightness variations associated with the indentation mark are hardly discriminatable from those associated with the flaw. Thus in the case of a golf ball having such an indentation mark, it is difficult to detect only the flaw 10 by the above-mentioned first inspection method.

It is the second inspection method that can detect only the flaw 10 on a golf ball having an indentation mark. More particularly, the outer appearance of a golf ball is inspected by the second inspection method as follows.

Figure 8:
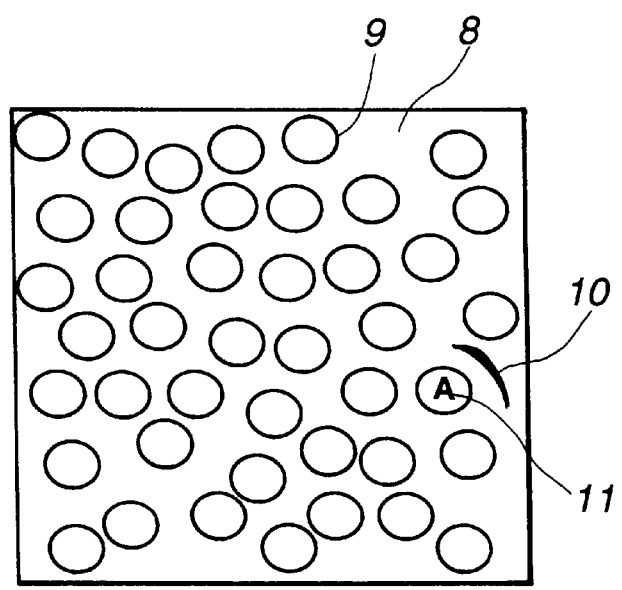
FIG. 8 is a two-dimensional image of a golf ball having an indentation mark.

While light is illuminated to a selected region of the golf ball 1 by means of the lighting means 3 and the golf ball 1 is rotated about an axis at a constant speed in one direction by means of the pair of rotating shafts 2, 2, the line sensor camera 4 is operated to take a series of plurality of line images of the ball surface in the selected region along a line b perpendicular to the rotational direction a. The camera delivers one-dimensional image data to the converter 5, which converts the data into a tow-dimensional image. Through appropriate image processing, there is obtained a two-dimensional image as shown in FIG. 8 wherein an indentation "A" appears at 11.

Next, as in the first inspection method, brightness changes along the rotational direction of the ball appearing on the two-dimensional image are converted into variations per preset unit, and the variation data is subjected to binary processing by setting a threshold between the variation associated with the dimple 9 and the variation associated with the flaw 10, thereby detecting the flaw 10. In the case of a ball having an indentation 11, portions of the ball surface where brightness variations are detected by binary processing as exceeding the threshold include not only the flaw 10, but also the indentation 11 as shown in FIG. 9.

Figure 9:
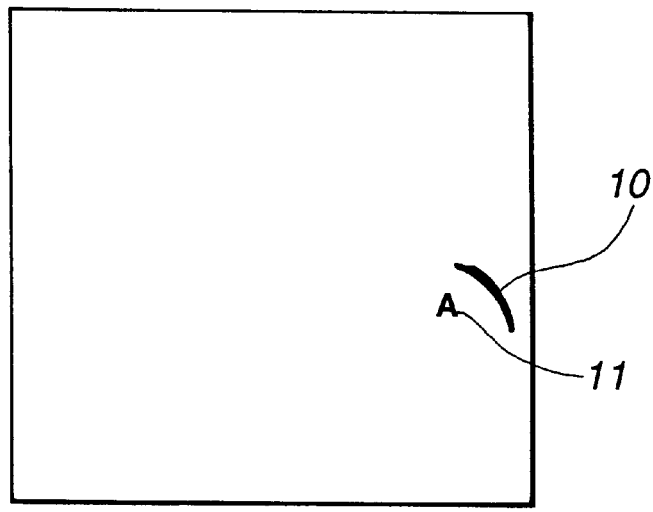
FIG. 9 is an image consisting of first image data obtained by converting the two-dimensional image of FIG. 8 into variation data and binarizing the variation data on the basis of a first threshold.
Figure 10:
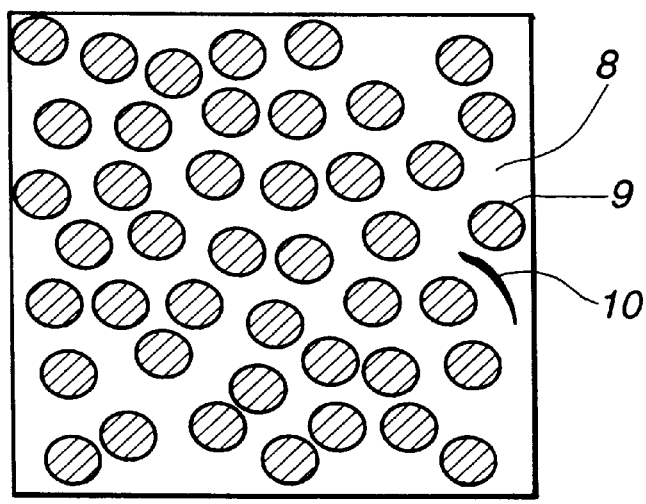
FIG. 10 is an image obtained by converting the tow-dimensional image of FIG. 8 into variation data and binarizing the variation data on the basis of a second threshold.

Then, according to the second inspection method, the first image data of FIG. 9 wherein the flaw 10 and the indentation 11 are represented as dark-in-light areas by the binary processing is obtained while the variation data is subject to binary processing by setting a second threshold between the variation associated with the land 8 and the variation associated with the dimple 9. Then as shown in FIG. 10, there is obtained an image wherein the dimples 9 and the flaw 10 presenting a greater variation than the dimple 9 are represented as dark-in-light areas under the background of the land 8. Where there is an indentation 11 in one dimple 9, the indentation 11 presents equal variations to the flaw 10, has the identical lightness with the dimple 9 and is thus hidden in the dimple 9. Particularly when the indentation 11 is a raised portion, the indentation 11 will present smaller variations like the land 8 and the indentation 11 will appear as a light-in-dark area in the dimple 9 as shown in FIG. 11A wherein the indentation 11 is illustrated as a white "A" in the black dimple circle 9.

Figure 11A:
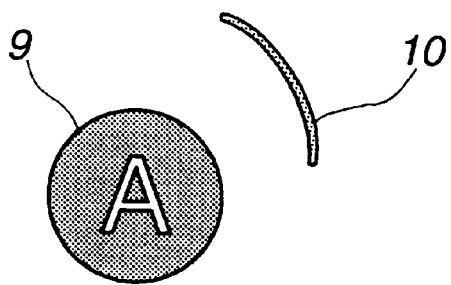
FIG. 11 illustrates the steps of expansion, contraction, and re-expansion.
Figure 11A:
Figure 11B:
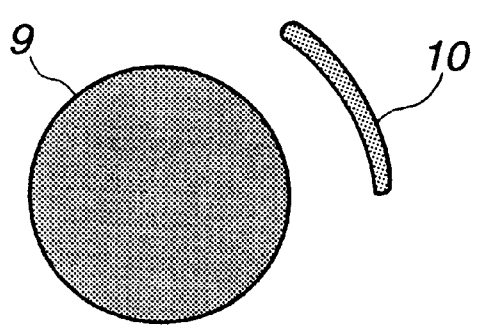
Figure 11B:
Figure 11C:
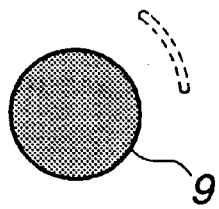
Figure 11C:
Figure 11D:
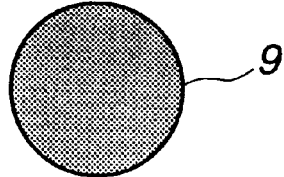
Figure 12:
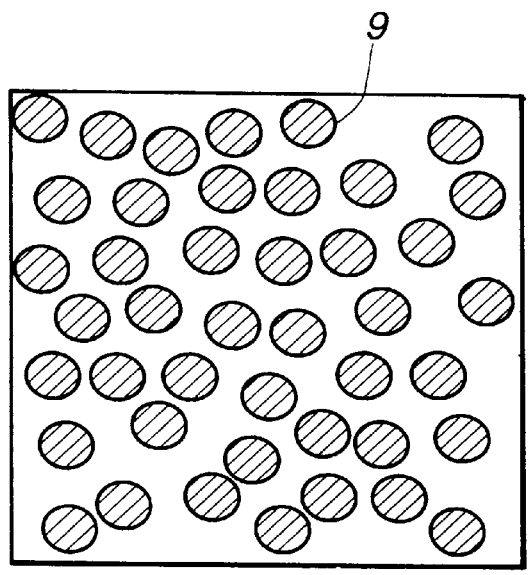
FIG. 12 is an image consisting of second image data obtained after the image resulting from binarization on the basis of a second threshold is subjected to expansion and contraction.

Next, as shown in FIG. 11, the light or dark areas representing the dimple 9 and the flaw 10 on the image of FIG. 10 (dark areas in the illustrated embodiment, the dark areas being black shaded in the figure) are expanded to extinguish the indentation which has been represented within the dimple 9 (FIG. 11A→FIG. 11B). Then the light or dark areas representing the dimple 9 and the flaw 10 (dark areas in the illustrated, embodiment) are contracted until the flaw 10 is extinguished (FIG. 11B→FIG. 11C) and thereafter, expanded again until the dimple 9 resumes the original size (FIG. 11C→FIG. 11D). As a result of this expansion and contraction procedure whereby the indentation 11 and the flaw 10 are extinguished, there is obtained a second image (or second image data) wherein only dimples 9 are represented as light or dark areas (dark areas in the illustrated embodiment) as shown in FIG. 12.

Figure 13:
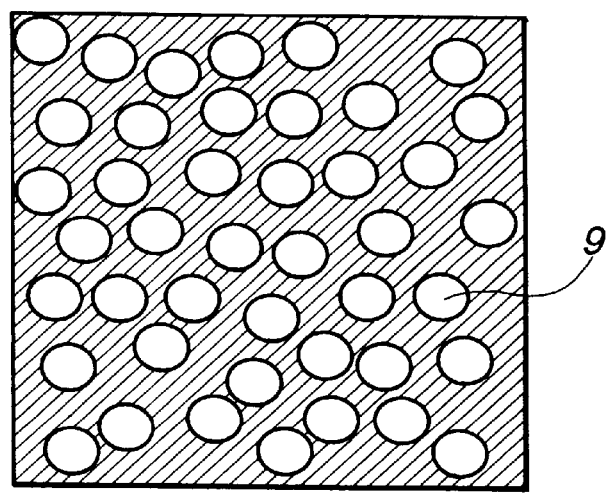
FIG. 13 is an image obtained by reversing the second image data.

Then the light and dark areas of the second image (or second image data) are reversed to form an image (or image data) wherein only the dimples 9 are represented as white areas in the black background as shown in FIG. 13. At this point, the second image (second image data) of FIG. 13 wherein only the dimples 9 are represented as white areas in the black background is laid on the first image (first image data) of FIG. 9 wherein the indentation 11 and flaw 10 are represented as black areas in the white background. Then, the indentation 11 (black) in the first image data (FIG. 8) overlaps the dimple 9 (white) in the second image data (FIG. 13), the flaw 11 (black) of the first image data (FIG. 8) overlaps the black background of the second image data (FIG. 13), and the white background of the first image data (FIG. 8) overlaps the dimples 9 or black background of the second image data (FIG. 13). In this state, the algorithm is designed to give preference to white where white and black areas overlap. Then all the areas become white except for the flaw 10 of black-black combination. This results in an image (image data) of FIG. 3 wherein only the flaw 10 is represented as a black area in the white background.

That is, the flaw 10 and indentation 11 appearing in FIG. 9 as detected by the binary processing based on the first threshold, the indentation 11 is extinguished and only the flaw 11 is detected through the above-mentioned series of image processing steps. Therefore, if a variation in excess of the first threshold is contained in the first image data represented in FIG. 9 after the image processing, then the ball surface is judged to contain a flaw. If a variation in excess of the first threshold is not contained in the first image data after the image processing, then the ball surface is judged to contain no flaw.

In this way, the second inspection method permits only a flaw to be detected on a golf ball having an indentation in a dimple since the indentation 11 is extinguished from the first image data by the series of image processing steps. When similar processing is done on a golf ball having no indentation, the detection of a flaw is not adversely affected. It is understood that the computer 6 shown in FIG. 1 can perform the series of image processing steps and the remaining construction is the same as in the first inspection method.

Although some preferred embodiments of the invention have been described, the method and apparatus for inspecting the outer appearance of golf balls according to the invention are not limited thereto and many modifications and variations may be made thereto in the light of the above teachings. For example, although the second image data are reversed after expansion/contraction processing in the illustrated embodiment of the second inspection method, the second image data may be reversed prior to expansion/contraction processing and the first image data may be reversed instead of the second image data. In the apparatus shown in FIG. 1, the monitor 7 is not essential and can be omitted. Although in the foregoing description, image processing is illustrated with reference to the drawings, the image obtained by processing need not necessarily be displayed as a visible image. The "image" may be a set of electrical data representing an image.

There has been described a method and apparatus for inspecting the outer appearance of golf balls which ensures that a defect is precisely discriminated from dimples so that only the defect may be precisely detected. According to the second inspection method, even when a golf ball has an indentation in a dimple, the defect is precisely discriminated from the indentation so that only the defect may be precisely detected.

I claim:

1. A method for inspecting the outer appearance of a golf ball having a multiplicity of dimples in its surface for detecting a defect on the ball surface, comprising the steps of illuminating light to a selected region of the golf ball, rotating the golf ball at a constant speed in one direction, operating a line sensor camera to take a series of plurality of line images of the ball surface in the selected region along a line perpendicular to the rotational direction at the same time as the illuminating and rotating steps, the camera delivering image data including the line images, constructing a two-dimensional image from the image data, converting a brightness change appearing in the tow-dimensional image in the rotational direction of the ball into a variation per preset unit, thereby obtaining variation data, and subjecting the variation data to binary processing on the basis of a threshold set between the variation associated with the dimple and the variation associated with the defect, thereby detecting whether or not the defect is present.

2. A method for inspecting the outer appearance of a golf ball having a multiplicity of dimples in its surface for detecting a defect on the ball surface, comprising the steps of illuminating light to a selected region of the golf ball, rotating the golf ball at a constant speed in one direction, operating a line sensor camera to take a series of plurality of line images of the ball surface in the selected region along a line perpendicular to the rotational direction at the same time as the illuminating and rotating steps, the camera delivering image data including the line images, constructing a two-dimensional image from the image data, converting a brightness change appearing in the two-dimensional image in the rotational direction of the ball into a variation per preset unit, thereby obtaining variation data, and subjecting the variation data to binary processing on the basis of a first threshold set between the variation associated with the dimple and the variation associated with the defect, thereby obtaining first image data representing the defect as a light or dark area, subjecting the variation data to binary processing on the basis of a second threshold set between the variation associated with the land and the variation associated with the dimple, thereby obtaining an image representing the defect and dimples as light or dark areas, subjecting the last-mentioned image to image processing, the image processing including the steps of expanding the defect- and dimple-representing areas, contracting the defect- and dimple-representing areas to extinguish the defect-representing area, and expanding again the dimple-representing areas to the original size, thereby obtaining second image data representing only the dimples as light or dark areas, overlapping the first image data and the second image data with the light and dark areas being reversed for one of the first image data and the second image data, and processing the overlapped data such that either one of light and dark areas is preferentially selected when light and dark areas are overlapped, thereby extinguishing areas other than the defect-representing area from the first image data, thereby detecting only the defect.

3. A method for inspecting the outer appearance of a golf ball according to claim 1 further comprising the step of removing from the region to be inspected any portion having a brightness below a predetermined level on the two-dimensional image constructed from the image data taken by the line sensor camera, thereby excluding a mark printed on the golf ball surface from the object to be detected.

4. An apparatus for inspecting the outer appearance of a golf ball having a multiplicity of dimples in its surface for detecting a defect on the ball surface, comprising a rotating means for holding and rotating the golf ball at a constant speed in one direction, a lighting means for illuminating light to a selected region of the golf ball, a line sensor camera adapted to take a series of plurality of line images of the ball surface in the selected region along a line perpendicular to the rotational direction, the camera delivering image data including the line images, a one to two-dimensional image converter means for constructing a two-dimensional image from the image data, an image converter means for converting a brightness change appearing in the two-dimensional image in the rotational direction of the ball into a variation per preset unit, and an image analysis means for subjecting the variation data to binary processing on the basis of a threshold, wherein said line sensor camera is operated to take a series of plurality of line images of the ball surface in the selected region along a line perpendicular to the rotational direction while light is illuminated to the selected region of the golf ball by said lighting means and the golf ball is rotated at a constant speed in one direction by said rotating means; said camera delivers image data including the line images to said one to two-dimensional image converter means, which constructs a two-dimensional image from the image data and delivers the image to said image converter means, which in turn, converts a brightness change appearing in the two-dimensional image in the rotational direction of the ball into a variation per preset unit and delivers the variation data to said image analysis means, which performs binary processing of the variation data on the basis of a threshold set between the variation associated with the dimple and the variation associated with the defect, thereby detecting whether or not the defect is present on the golf ball surface.

5. An apparatus for inspecting the outer appearance of a golf ball having a multiplicity of dimples in its surface for detecting a defect on the ball surface, comprising a rotating means for holding and rotating the golf ball at a constant speed in one direction, a lighting means for illuminating light to a selected region of the golf ball, a line sensor camera adapted to take a series of plurality of line images of the ball surface in the selected region along a line perpendicular to the rotational direction, the camera delivering image data including the line images, a one to two-dimensional image converter means for constructing a two-dimensional image from the image data, an image converter means for converting a brightness change appearing in the two-dimensional image in the rotational direction of the ball into a variation per preset unit, an image analysis means for subjecting the variation data to binary processing on the basis of a threshold, and an image processing means for receiving the two-dimensional image consisting of light and dark areas and expanding and contracting the light or dark areas, wherein said line sensor camera is operated to take a series of plurality of line images of the ball surface in the selected region along a line perpendicular to the rotational direction while light is illuminated to the selected region of the golf ball by said lighting means and the golf ball is rotated at a constant speed in one direction by said rotating means; said camera delivers image data including the line images to said one to two-dimensional image converter means, which constructs a two-dimensional image from the image data and delivers the image to said image converter means, which in turn, converts a brightness change appearing in the two-dimensional image in the rotational direction of the ball into a variation per preset unit and delivers the variation data to said image analysis means, which performs binary processing of the variation data on the basis of a threshold set between the variation associated with the dimple and the variation associated with the defect to thereby produce first image data representing the defect on the ball surface as a light or dark area, said image analysis means also performs binary processing of the variation data on the basis of a second threshold set between the variation associated with the land and the variation associated with the dimple to thereby produce an image representing the defect and dimples as light or dark areas, and delivers the last-mentioned image to said image processing means, which performs image processing including the steps of expanding the defect- and dimple-representing areas, contracting the defect- and dimple-representing areas to extinguish the defect-representing area, and expanding again the dimple-representing areas to the original size, thereby producing second image data representing only the dimples as light or dark areas, said apparatus further including a processing means for overlapping the first image data and the second image data with the light and dark areas being reversed for one of the first image data and the second image data, and processing the overlapped data such that either one of light and dark areas is preferentially selected when light and dark areas are overlapped, thereby extinguishing areas other than the defect-representing area from the first image data, thereby detecting only the defect.

* * * * *